United States Patent
DuBois et al.

(10) Patent No.: US 9,610,023 B2
(45) Date of Patent: *Apr. 4, 2017

(54) SYSTEM AND METHODS FOR COMPUTING ACTIVATION MAPS

(71) Applicant: CARDIOINSIGHT TECHNOLOGIES, INC., Cleveland, OH (US)

(72) Inventors: Remi DuBois, Paris (FR); Harold Wodlinger, Thornhill (CA); Charulatha Ramanathan, Solon, OH (US); Brian P. George, Cleveland, OH (US); Pierre Roussel-Ragot, Paris (FR)

(73) Assignee: CARDIOINSIGHT TECHNOLOGIES, INC., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/964,707

(22) Filed: Dec. 10, 2015

(65) Prior Publication Data

US 2016/0095530 A1 Apr. 7, 2016

Related U.S. Application Data

(63) Continuation of application No. 13/829,631, filed as application No. PCT/US2011/051954 on Sep. 16, 2011, now Pat. No. 9,271,680.

(Continued)

(51) Int. Cl.
*A61B 5/04* (2006.01)
*A61B 5/00* (2006.01)
(Continued)

(52) U.S. Cl.
CPC ........ *A61B 5/04012* (2013.01); *A61B 5/0044* (2013.01); *A61B 5/042* (2013.01);
(Continued)

(58) Field of Classification Search
CPC .............. A61B 5/0044; A61B 5/04011; A61B 5/04012; A61B 5/042; A61B 5/0422;
(Continued)

(56) References Cited

U.S. PATENT DOCUMENTS

| 5,054,496 A | 10/1991 | Wen et al. |
| 6,574,492 B1 * | 6/2003 | Ben-Haim ........... A61B 5/0215 600/374 |

(Continued)

FOREIGN PATENT DOCUMENTS

| EP | 1070480 A2 | 1/2001 |
| WO | 9724983 A2 | 7/1977 |
| WO | 2006037172 A1 | 4/2006 |

OTHER PUBLICATIONS

International PCT Patent Application Search Report and Written Opinion, Applicant: Cardioinsight Technologies, Inc., International PCT Application No. PCT/US2011/051954, Filing Date: Sep. 16, 2011; Authorized Officer: Suang Chan Chung; Date of Actual Completion: Apr. 20, 2012; 7 pgs.

(Continued)

*Primary Examiner* — George Manuel
(74) *Attorney, Agent, or Firm* — Tarolli, Sundheim, Covell & Tummino LLP

(57) ABSTRACT

Systems and methods can be used to determine activation information for points along a surface or selected region of interest. In one example, a computer-readable medium having computer-executable instructions for performing a method that includes computing a local activation vector based on relative timing among electrical signals corresponding to neighboring points of a plurality of points on a surface envelope. An activation time can be computed for each of the plurality of points as a function of corresponding local activation vectors.

20 Claims, 7 Drawing Sheets

Related U.S. Application Data

(60) Provisional application No. 61/482,290, filed on May 4, 2011, provisional application No. 61/383,945, filed on Sep. 17, 2010.

(51) Int. Cl.

| | | |
|---|---|---|
| *A61B 5/044* | (2006.01) | |
| *A61B 5/0452* | (2006.01) | |
| *A61B 5/0478* | (2006.01) | |
| *A61B 5/042* | (2006.01) | |
| *G06F 19/00* | (2011.01) | |

(52) U.S. Cl.
CPC .......... *A61B 5/044* (2013.01); *A61B 5/04011* (2013.01); *A61B 5/0452* (2013.01); *A61B 5/0478* (2013.01); *A61B 5/6823* (2013.01); *A61B 5/7271* (2013.01); *A61B 5/743* (2013.01); *A61B 5/0422* (2013.01); *G06F 19/3437* (2013.01)

(58) Field of Classification Search
CPC ..... A61B 5/044; A61B 5/0452; A61B 5/0478; A61B 5/6823; A61B 5/7271; A61B 5/743; G06F 19/3437
See application file for complete search history.

(56) References Cited

U.S. PATENT DOCUMENTS

| | | |
|---|---|---|
| 2002/0151808 A1 | 10/2002 | Schwartzman et al. |
| 2007/0161915 A1 | 7/2007 | Desai |
| 2009/0088655 A1 | 4/2009 | Vajdic et al. |

OTHER PUBLICATIONS

Supplementary European Search Report, Applicant: Cardioinsight Technologies, Inc., European Application No. 11626029, Filing Date: Sep. 16, 2011; Examiner: L. Mendelevitch; Date of Completion: Nov. 24, 2015; 7 pgs.

International PCT Patent Application Search Report and Written Opinion, Applicant: Cardioinsight Technologies, Inc., International PCT Application No. PCT/US2011/051954; Filing Date: Sep. 16, 2011; Authorized Officer: Suang Chan Chung; Date of Actual Completion: Apr. 20, 2012; 7 pgs.

\* cited by examiner

SYSTEM AND METHODS FOR COMPUTING ACTIVATION MAPS

CROSS-REFERENCE TO RELATED APPLICATIONS

This application is a Continuation of U.S. patent application Ser. No. 13/829,631, filed Mar. 14, 2013, and entitled SYSTEM AND METHODS FOR COMPUTING ACTIVATION MAPS, which is a U.S. National Stage Application of PCT/US2011/051954, having an international filing date of Sep. 16, 2011, which claims the benefit of priority from U.S. Provisional Patent Application No. 61/482,290, filed on May 4, 2011, and entitled SYSTEM AND METHODS FOR COMPUTING ACTIVATION MAPS, and U.S. Provisional Patent Application No. 61/383,945, filed on Sep. 17, 2010, and entitled SYSTEM AND METHODS FOR COMPUTING ACTIVATION MAPS. The entire contents of each of the above-identified patent applications are incorporated herein by reference.

TECHNICAL FIELD

This disclosure relates to systems and methods for computing activation maps.

BACKGROUND

Electroanatomical mapping is a broad term that covers several modes of mapping for a body surface, such as the heart. Some examples of cardiac mapping are endocardial mapping and epicardial mapping. The mapping can be utilized to generate an image, such as an isochronal image, for displaying electrophysiological information. One type of cardiac map is an activation map, which can be used to display activation time patterns on a surface of the heart.

For example, the activation time for a given location can be determined as the maximum negative slope (dV/dt) in the signal. This common approach fails to account for the relationships between near-field and far-field components of signals as well as other potential anatomical features that may cause signal artifacts. As a result, such an approach can result in an inaccurate map being constructed. This approach also tends to be extremely sensitive to noise.

SUMMARY

This disclosure relates to systems and methods for computing activation maps.

One example provides a computer-readable medium having computer-executable instructions for performing a method that includes computing a local activation vector based on relative timing among electrical signals corresponding to neighboring points of a plurality of points on a surface envelope. An activation time can be computed for each of the plurality of points as a function of corresponding local activation vectors.

Another example provides a method that includes computing, by a processor, a global activation time for a plurality of points of a cardiac surface envelope based on analysis of signals at neighboring points of the plurality of points over the cardiac surface envelope. An output can be generated based on the global activation time computed for the plurality of points of the cardiac surface envelope.

DETAILED DESCRIPTION

This disclosure relates to systems and methods to determine activation time. The systems and methods can be employed to generate an activation map for electrical activity on a surface of an anatomical structure, such as including the body surface, a muscle, or organ. In one embodiment, the system and methods can be utilized to generate an activation map for a surface of a patient's heart, such as can be an epicardial surface, an endocardial surface or another cardiac envelope.

By way of example, activation data can be computed based on a comparison of neighboring electrical signals for points on a surface of the anatomical structure. The surface can be the entire surface or a portion of the surface. For instance, local activation vectors can be computed based on an analysis of signals at neighboring points over the surface. The neighboring points can include two or more contiguous neighboring points on the surface (e.g., the nearest neighbors). As one example, the analysis can include comparing time delays computed from the signals (e.g., electrograms) at neighboring points. The neighboring points can include two or more adjacent points, such as in an identified region of the surface. The local activation vectors can be employed to compute the activation time for neighboring points in an iterative manner until the activation time has been computed for each or a selected subset of the points. This approach can be referred to as a directional activation algorithm since it involves analysis relating to the direction of the activation.

As a further example, a hybrid approach can be utilized in which the directional activation algorithm is implemented in conjunction with another, different type of activation time computation, such as can correspond to computing the maximum negative slope (dV/dt) of the signal at each of the points. The results from both approaches can be aggregated to provide the activation time for each or a selected subset of the points on the surface. For example, the activation times from this other approach can constrain or otherwise modify the directional activation algorithm.

Figure 1:
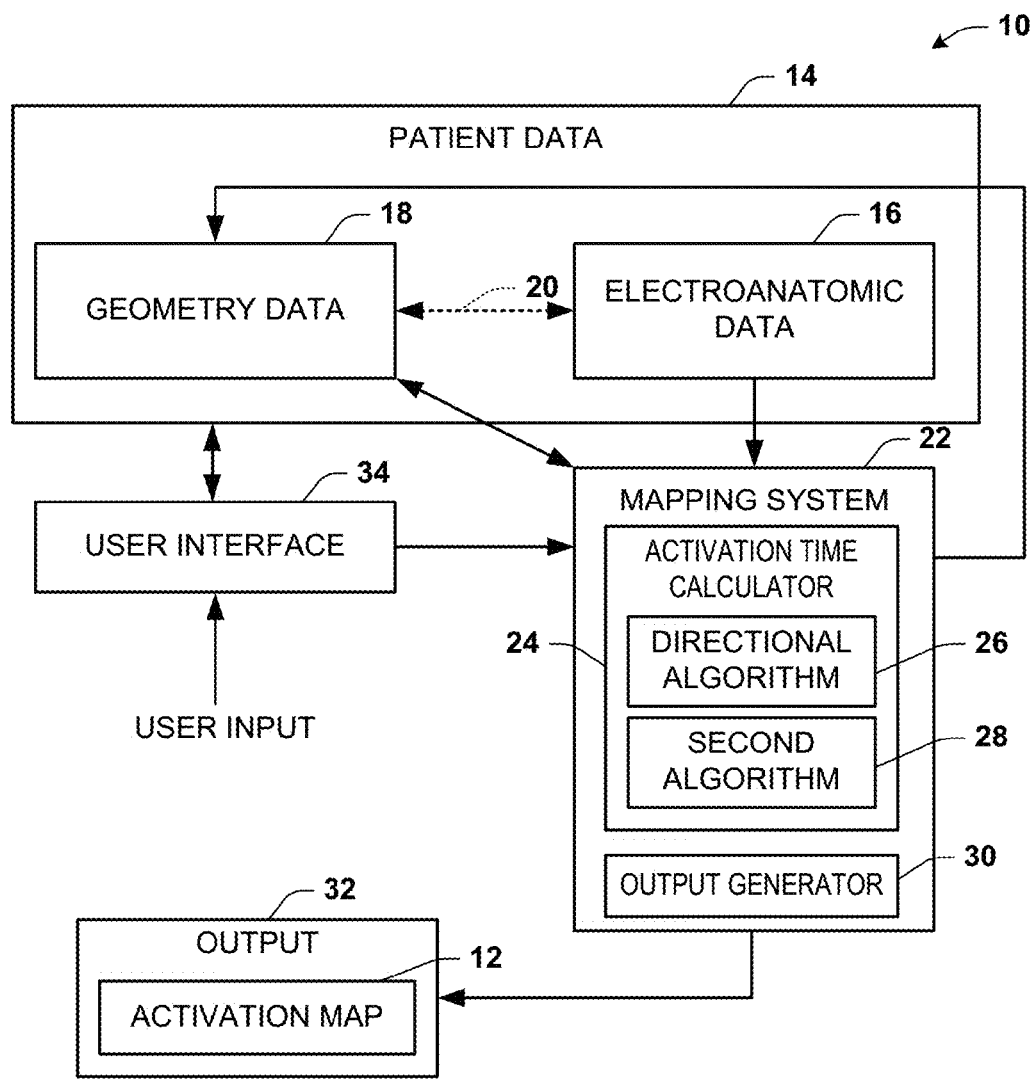
FIG. 1 depicts an example of a system that can be implemented to determine activation map data.

FIG. 1 depicts an example of a system 10 for computing activation data, such as for generating an activation map 12. The system 10 can be implemented in a standalone computer, a workstation, an application specific machine, or in a network environment in which one or more of the modules or data can reside locally or remotely relative to where a user interacts with the system 10.

The system 10 employs patient data 14 for one or more patient, such as can be stored in an associated memory device (e.g., locally or remotely). The patient data 14 can include electroanatomic data 16 that represents electrical information for a plurality of points, each of which is indexed or otherwise programmatically associated with (e.g., linked to) a surface model. The patient data 14 can also include geometry data 18, such as can be embodied as a patient geometry model for a given patient. In one embodiment, the patient geometry data can correspond to a surface of model of a patient's entire organ, such as the heart, brain or other muscle, which can be graphically rendered as a two- or three-dimensional representation. Alternatively, the geometry data can correspond to a generic model of a surface of the heart or other anatomical structure, such as can be derived from geometry data acquired for one or more patients.

The patient electroanatomic data 16 can be raw data, such as has been collected from an electrophysiology mapping catheter or other means that can be utilized to acquire electrophysiology data for a selected region of a patient (e.g., of an organ, such as the heart). Additionally or alternatively, the electroanatomic data 16 can correspond to processed data, such as can be computed from raw data to provide electrophysiology information for the selected anatomical structure of the patient (e.g., a surface of the heart).

By way of example, non-invasive electrophysiological mapping (e.g., electrocardiographic (EC) mapping for the heart) can be performed on the patient to generate the electroanatomic data 16. This technique can generate electrophysiological data by combining body surface electrical measurements with geometry information through an inverse computation programmed to reconstruct the electrical activity for a predetermined surface envelope, such as for a cardiac surface envelope. The cardiac surface envelope can refer to an epicardial surface envelope that is on or outside the epicardial cardiac surface that at least partially encloses the epicardial cardiac surface or to an endocardial surface envelope that is within the epicardial surface. Thus, the results of the inverse computation can provide the corresponding electroanatomic data 16 that is registered with the geometry data 18, thereby providing electrical potentials concurrently for each of a plurality of points on the cardiac surface envelope (or other surface construct).

In another example, a contact or non-contact electrophysiology catheter can be placed in a patient's heart and collect electrophysiology data at a plurality of spatial locations over time, such as during a number of one or more cardiac intervals. Such data can be spatially and temporarily aggregated in conjunction with image data for the patient's heart to provide the electroanatomic data 16 for corresponding regions of the patient's heart. Alternatively, other devices (e.g., catheters or patches) can be placed on or near a patient's heart, endocardially and/or epicardially, such as during open chest and minimally invasive procedures, to record electrical activity data, which can be mapped to a cardiac surface envelope to provide similar corresponding electroanatomic data 16.

Those skilled in the art will understand and appreciate that the system 10 is equally applicable to patient electroanatomic data 16 that can be gathered and/or derived by any of these or other approaches, which may be invasive, non-invasive or a combination of invasive and non-invasive procedures. Additionally, it will be understood and appreciated that the electroanatomic data 16 can be provided in any form and converted into an appropriate form for processing in the system 10. The patient data 14 can be stored in memory for processing off-line. Alternatively or additionally, the patient data 14 can be stored as part of a real-time monitoring procedure that displays the activation map 12 concurrently with the measurement of patient electrical data.

In addition to the patient electroanatomic data 16 related to the patient's organ, the system 10 can also employ the geometry data 18, such as to graphically represent a predetermined surface region of an anatomical structure, such as corresponding to that of a patient or a generalized model. For example, the geometry data 18 can correspond to a patient-specific representation of a surface of an organ or other structure to which the patient electroanatomical data has been co-registered. For instance, the geometry data 18 may include a graphical rendering of a model region of the patient's organ, such as can be generated by appropriate imaging processing methods based on image data acquired for the patient. Such image processing can include extraction and segmentation of an organ from a digital image set. The segmented image data thus can be converted into a two-dimensional or three-dimensional graphical representation of a surface region of the patient's organ. Alternatively, the geometry data 18 can correspond to a mathematical model of the patient's organ that has been constructed based on image data for the patient's organ or any model of it. As another alternative, the geometry data can represent a generic model of a surface of an organ. Such a generic model can be co-registered with patient image data to facilitate generating the activation map 12 as well as other outputs for the patient. Appropriate anatomical or other landmarks can be associated with the organ represented by the anatomical data for the organ to facilitate subsequent processing and visualization in the system 10.

As one example, the geometry data 18 comprises a surface model that represents a surface of the anatomical structure (e.g., a surface of a heart). The surface model can define a mesh, which includes a collection of vertices that define a plurality of polygons forming the surface. Each polygon can include three or more vertices, such that adjacent vertices define edges that surround a face of each respective polygon (see, e.g., FIG. 8).

As mentioned above, the electroanatomic data 16 can be registered into a common coordinate system with the geometry data 18. For example, the electroanatomic data 16 can be stored in a data structure of rows (corresponding to different anatomical points) and columns (corresponding to samples) in which the rows of data have the same index as (or are registered to) respective points residing on geometry data 18. This registration or indexed relationship between the electrical data and the geometry data 18 is schematically depicted in FIG. 1 by a dashed line 20. In one example, the samples in each of the columns can represent simultaneous electrical information across the entire surface region (or a portion of the surface) of the anatomical structure (e.g., the heart) for the patient.

The geometry data 18 can be generated from image data that is acquired using nearly any imaging modality. Examples of imaging modalities include ultrasound, computed tomography (CT), 3D Rotational angiography (3DRA), magnetic resonance imaging (MRI), x-ray, positron emission tomography (PET), and the like. Such imaging can be performed separately (e.g., before or after the measurements) utilized to generate the electroanatomic data 16. Alternatively, imaging may be performed concurrently with recording the electrical activity that is utilized to generate the patient electroanatomic data 16.

It will be understood and appreciated by those skilled in the art that the system 10 is equally applicable to employ anatomical data that may be acquired by any one of these or other imaging modalities. The type of imaging modality can vary according to the purpose or purposes of the data 18. For example, CT provides an effective modality for use in performing the inverse method in conjunction with body surface electrodes used in performing electrical measurements for generating the electroanatomic data 16 as EC mapping data. Thus, one or more image sets can be acquired and co-registered, which can be collectively stored as the geometry data 18.

Alternatively or additionally, the geometry data 18 can correspond to a generic or custom representation of an organ, which may not be the patient's own organ. In such a case, the electroanatomic data 16 can be mapped (via registration process) to the representation of the organ according to identified anatomical landmarks. A manual, semi-automatic or automatic registration process can be employed in order to register the anatomical model with the signal acquisition system, if any. As a further example, the geometry data can correspond to patient anatomy that is constructed by 3D localization of a mapping catheter. For instance, as a mapping catheter is moved around a desired anatomical region (e.g., a heart chamber), both the anatomical model and the electrical maps can be built in a point-by-point manner.

It further will be understood and appreciated that depending upon the format and type of input data appropriate formatting and conversion to a corresponding type of representation can be implemented by the system 10. For instance, the patient data 14 can include electroanatomical data that is provided to the system 10 in a known format or be converted to a standard format for processing by the system. Thus, the patient data 14 can include an aggregate set of electroanatomical data for the patient.

The system 10 also includes a mapping system 22 is programmed to generate one or more different types of output maps including the activation map 12. The mapping system 22 includes an activation time calculator 24 programmed compute activation time data based on the electroanatomic data 16. The mapping system 22 generates the activation map based on the activation time data.

The activation time calculator 24 can employ a directional activation algorithm 26 programmed to compute activation time based on estimating a direction of activation for signals across the surface. For example, the direction of activation can be derived based on time delays between the neighboring signals across the surface. Based on the direction of activation and relative timing between signals at different points, activation time can be calculated over the entire surface or a selected portion of the surface (e.g., the heart or another envelope). The mapping system 22 compares neighboring temporal electrical signal to locally exhibit a direction of the activation. Performed on the entire heart surface, the mapping system 22 can provide a global activation map.

Additionally, the activation time calculator 24 can be programmed to employ a hybrid algorithm that employs plural methods for computing activation time. In one example, the hybrid method can employ the directional activation algorithm 26, such as disclosed herein, and one or more second algorithm, demonstrated at 28. As one example, the second algorithm 28 can be applied selectively to a subset of electrograms, corresponding a proper subset of points on the surface. The second algorithm can detect those electrograms (e.g., monophasic electrograms) that meet predefined criteria to help ensure that the second activation time computation can quantitatively reliably determine the activation time. For example, the second algorithm can compute the activation time as the point of maximum negative derivative ($-dV/dt_{max}$) of the QRS segment in each electrogram on the surface of interest. In one example, the activation times computed by the second algorithm 28 (presumed to be reliable) can be utilized without modification for activation times for the selected set of points on the surface and the directional algorithm can provide the activation time for the other points on the surface. Alternatively, the directional algorithm 26 and the second algorithm can be combined to provide an aggregate system of equations, including equations from the directional algorithm for each of points on the surface and equations at the reliable points. The time calculator 24 can solve the aggregate system of equations to obtain the activation time for each of the points on the surface concurrently.

An output generator 30 is programmed to generate an output 32, such as can include the activation map 12. The activation map 12 can be provided as including an isochrone map for the entire surface (e.g., in three dimensions) or a selected region of the surface. As mentioned above, for the example of a heart an electrogram signals, the surface can correspond to an epicardial surface envelope or another cardiac surface envelope.

The system 10 can also include a user interface 34 that can be utilized to activate or control the mapping system 22. The user interface 34 can provide a graphical and/or other interface that allows a user to provide a user input for initiating the process of generating an activation map. The user interface 34 can also be utilized to set and establish data paths and variables. The user interface 34 can also be utilized to configure the mapping system 22 or selecting a surface area for which the map is generated, for example.

Figure 2:
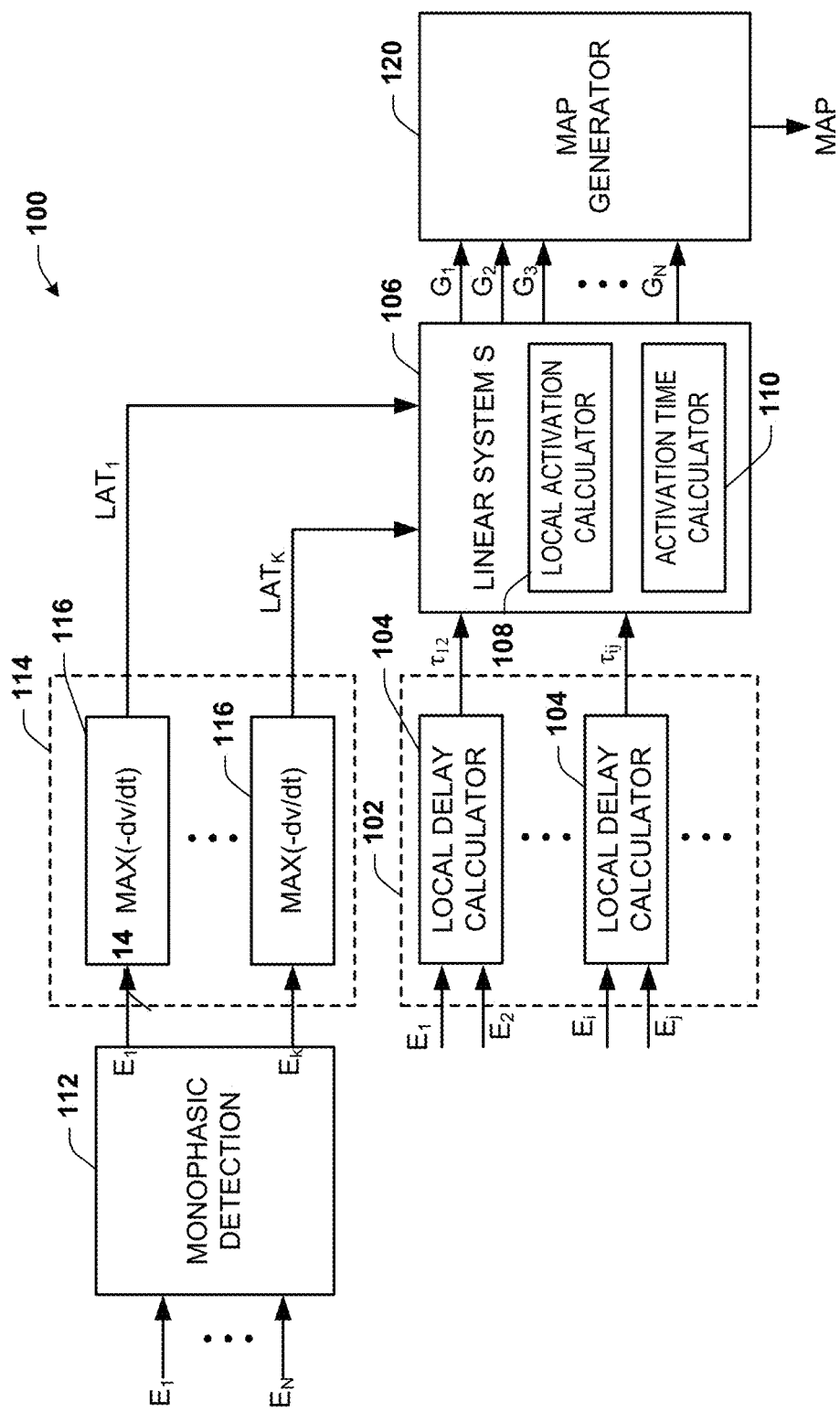
FIG. 2 depicts an example of time calculation system that can be programmed to compute global activation time.

FIG. 2 demonstrates an example of an activation time calculation system 100 that can be implemented to determine global activation times for a plurality of points, such as residing on a surface envelope. The system 100 can be implemented as computer readable instructions stored in memory, which can be executed by a processing unit. The activation time calculator can be implemented as the activation time calculator 24 disclosed in FIG. 1 and reference can be made back to FIG. 1 for additional context.

As an example, let $X_1, X_2, \ldots, X_N$ represent N different locations or points distributed across a surface of the anatomical structure or region of interest, where N is a positive integer denoting the number of points on the surface (e.g., N). Each point $X_1, X_2, \ldots, X_N$ can correspond to vertices of one or more polygons on the surface. For a given signal at each respective location, let the $\{s_i\}_{i=1\ldots N}$ represent the temporal activity of each respective signal at each location $X_i$. As an example, each signal may be an electrogram, such as demonstrated in FIG. 3 as $E_1$ through $E_N$. Each of the electrograms $E_1$ through $E_N$ can be measured or reconstructed for each of the N points (e.g., endocardial or epicardial locations) on a surface 50.

Figure 3:
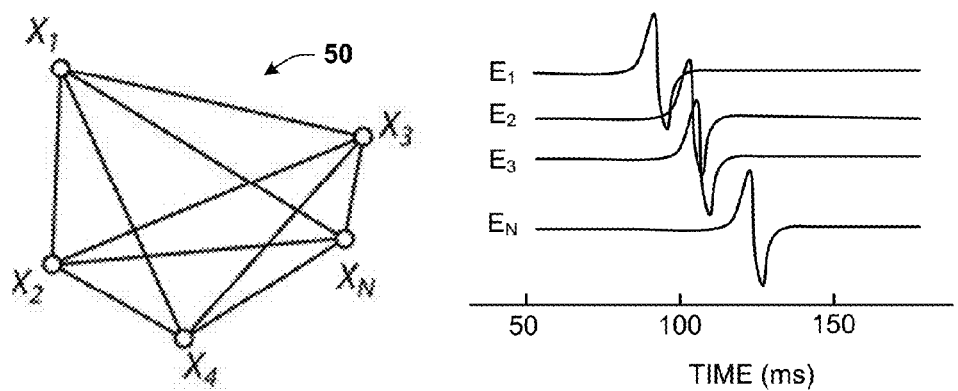
FIG. 3 depicts an example of a portion of a surface envelope and sample signals for points along such surface.
Figure 4:
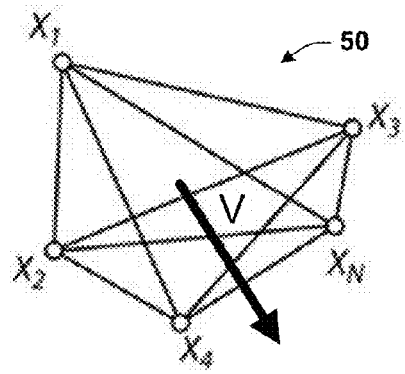
FIG. 4 depicts an example of neighboring points along a surface demonstrating a local activation vector that can be computed from signals at such points.

The activation time calculation system 100 thus can implement methods to compute activation vectors for a set of neighboring points, such as the vector V demonstrated in the example of FIG. 4 for the same points $X_1, X_2, \ldots, X_N$ demonstrated in FIG. 3. The system 100 can include a time delay calculator 102 that is programmed to determine a time delay between signals for pairs of points on the surface, such as for each adjacent pair of neighboring points on the surface of the structure. As mentioned, the points on the surface can correspond to vertices of a polygonal surface model that represents the surface of interest. The points (e.g., vertices) and corresponding electrical signals for such points can be computed from the electroanatomic data (e.g., the electroanatomic data 16 in FIG. 1).

By way of example, the points and corresponding electrical signals $E_1$ through $E_N$ can be derived by combining measured electrical data with the patient geometry data through an inverse algorithm to reconstruct the electrical activity onto corresponding points of a surface representation (e.g., a three-dimensional representation) of the patient's organ. This process is known as electrocardiographic mapping or imaging. Examples of inverse methods suitable for use with body surface electrodes are disclosed in U.S. Pat. No. 6,772,004, entitled System and Method for Non-invasive Electrocardiographic Imaging and U.S. Pat. No. 7,983,743, entitled System and method for noninvasive electrocardiographic imaging (ECGI), both of which are incorporated herein by reference. It will be appreciated that other approaches can be utilized to derive the electroanatomic data, which further may vary according to the mechanism utilized to acquire the patient electroanatomic data.

The calculations to derive the electrogram data for the points on the surface can be implemented as part of the methods used by the activation time calculation system 100 for determining the activation time data. Alternatively, the electrogram data on the surface, e.g., corresponding to signals $E_1$ through $E_N$ can be computed by separate methods to include the electrogram data for the points on the surface region (e.g., epicardial or endocardial surface) of the patient's heart.

Figure 5:
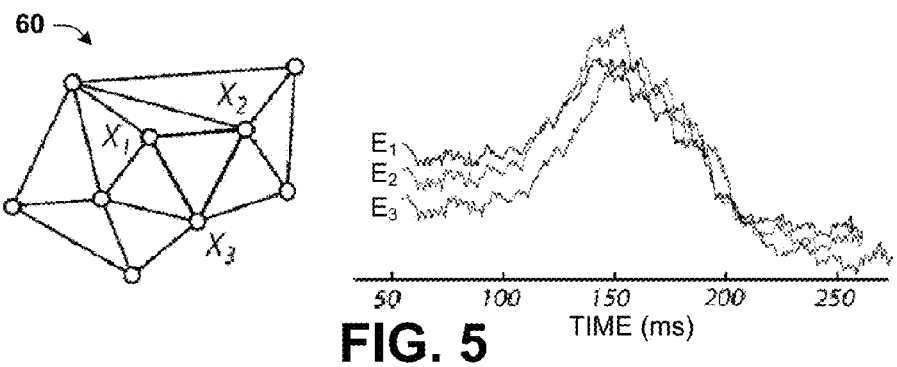
FIG. 5 depicts an example of points of a cardiac surface envelope and sample electrogram signals for such points.

As a further example, FIG. 5 depicts a portion of a mesh surface 60 that includes a polygon having vertices X1, X2 and X3. Electrogram signals $E_1$, $E_2$ and $E_3$ have been determined for each of the points on the polygon as shown. For the example of a triangle, three time delays between the three signals at each of the vertices are computed. While the polygon is depicted as a triangle, it will be appreciated that the mapping system 22 can employ polygons can have any number of vertices.

The time delay calculator 102 can include local delay calculators 104 programmed to compute the time delay between electrogram signals for each of the neighboring points, such as corresponding to any two nearby vertices in the surface mesh. As one example, the neighboring points can correspond to vertices along a common edge for each polygon in the surface mesh. The local delay calculator 104 can provide the time delay $\tau_{i,j}$ between a sampled signal $E_i$ measured for point $X_i$ and the same impulse $\langle .|. \rangle$ $E_j$ measured for a different neighboring location $X_j$. For example, the local delay calculators 104 can compute the measurement of the time delay between two neighboring signals $E_i$ and $E_j$ via a cross-correlation coefficient sequence $R_{s_i,s_j}$ between the two signals, such as follows:

$$R_{s_i,s_j}(t) = \frac{1}{R_{s_i,s_j}(0)} \sum_{k=0}^{N-t} s_i(k+t)s_j(k)$$

The time delay can thus be defined as the time $\tau_{i,j}$ at which $R_{s_i,s_j}$ reaches its maximum, such as follows:

$$\tau_{i,j} / R_{s_i,s_j}(\tau_{i,j}) = \max_t (R_{s_i,s_j}(t))$$

An underlying assumption is that the shape of the signal is not too different from one vertex to a neighboring vertex, and that only a time shift is observed between each pair of neighboring signals.

As an alternative to the computation of the cross correlation coefficient described above, local delay calculators 104 can employ a derivative based solution to compute the time delays, such as set forth in the following example.

Let $\tau_{ij}$ be the time delay to be evaluated between two points $X_i$ and $X_j$.

Let $s_i$ and $s_j$ be the corresponding EGMs respectively related to the $X_i$ and $X_j$.

Let $T_i^d$ be the time when the derivative of $s_i(t)$ is minimum:

$$T_i^d / \frac{ds_i}{dt}(T_i^d) = \min_t \frac{ds_i}{dt}(t)$$

Let $T_j^S$ be the time when the signal $s_j(t)$ is equal to the value of $s_i(T_i^d)$:

$$T_j^S/s_j(T_j^S)=s_i(T_i^d)$$

Let $T_j^d$ be the time when the derivative of $s_j(t)$ is minimum:

$$T_j^d / \frac{ds_j}{dt}(T_j^d) = \min_t \frac{ds_j}{dt}(t)$$

Let $T_i^S$ be the time when the signal $s_i(t)$ is equal to the value of $s_j(T_j^d)$:

$$T_i^S/s_i(T_i^S)=s_j(T_j^d)$$

From the foregoing, the time delay $\tau_{ij}$ can be computed as follow:

$$\tau_{ij}=\frac{1}{2}[(T_j^d-T_i^S)+(T_j^S-T_i^d)]$$

Returning to FIG. 2, the activation time calculation system 100 can also employ a linear system 106 that can provide a system of equations that are solved to obtain the activation time for each of the points on the surface, demonstrated as $G_1$ through $G_N$. For example, the linear system S 106 can employ a local activation calculator 108 that is programmed with equations to compute a local activation vector for each polygon on the surface. The local activation calculator 108 can compute the local activation vector based on the time delays determined by the time delay calculators 104, such as disclosed herein.

As an example, the local activation calculator 108 can compute a local activation vector for each polygon on the surface. For instance, let V represent the vector that represents the activation vector in this area. An estimate of V can be obtained from the following equations:

$$\langle V|X_j-X_i \rangle =\tau_{ij} \text{ for } \{(i,j)|i=1 \ldots N, j=1 \ldots N, j>i\}$$

where $\langle .|. \rangle$ is the dot product

In two-dimensions, one can write $$V = \begin{Bmatrix} V_x \\ V_y \end{Bmatrix} \text{ and } X_i = \begin{Bmatrix} x_i \\ y_i \end{Bmatrix}$$

for all i; and the above system can thus be written as $$\frac{N(N-1)}{2}$$

equations with two unknowns, $V_x$ and $V_y$.

Here, N is greater than two so the system is over determined. As one example, the solution for the unknowns $V_x$ and $V_y$ can be computed by a least mean square approach, which leads to a solution which minimizes the sum of the square of the errors made in solving each equation.

Following the method, a quality index Q equal to the sum of mean square errors between the solution and all equations can be computed. A large value for the Q index is therefore related to a decrease in the quality of the solution obtained, whereas a small Q index corresponds to an increase in quality.

Figure 6:
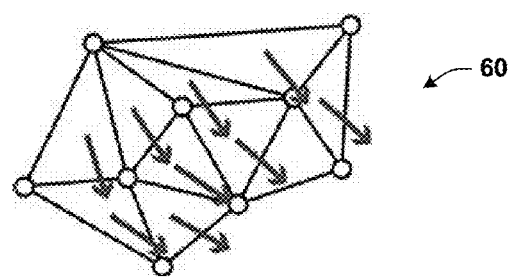
FIG. 6 depicts an example of a portion of a surface envelope and local activation vectors that can be computed for polygons corresponding to such points.
Figure 7:
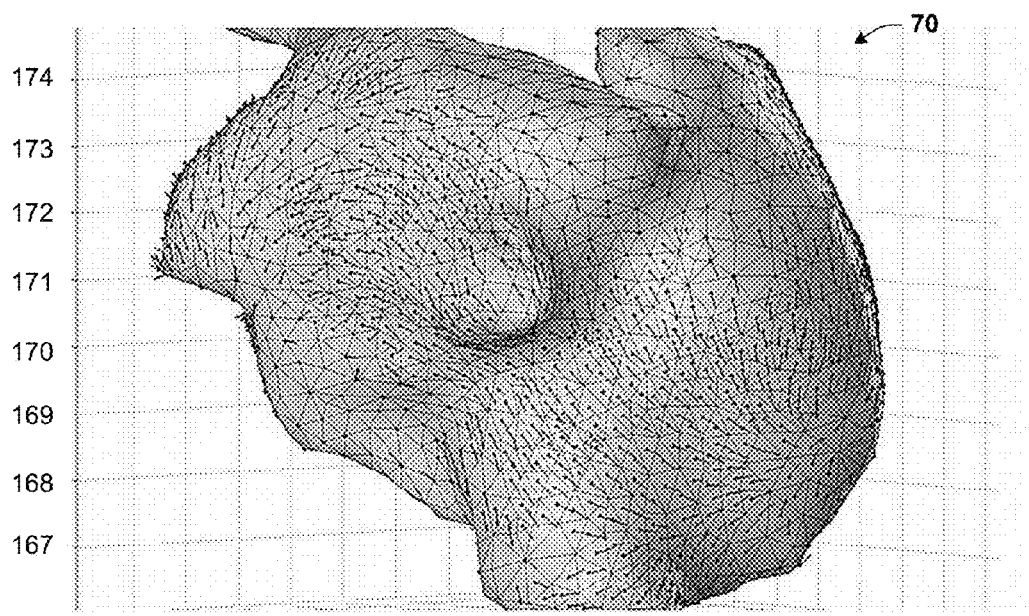
FIG. 7 depicts an example of a propagation pathway, including location activation vectors, such as can be computed for a surface region of a heart.

The local activation calculator 108 can apply this computation on every polygon which is part of the mesh surface, such as to provide an indication of the global activation pathway over the whole surface region of interest, such as demonstrated for a portion of the surface 60 in FIG. 6. That is, FIG. 6 demonstrates an example of local propagation pathways that can be computed by the local activation calculator 26 by the computation of the activation vector for each polygon in the mesh surface of interest. FIG. 7 depicts a further example of local activation times that can be computed on the posterior face of atria 70 demonstrating the corresponding propagation pathway.

Returning to the example of FIG. 2, the linear system S 106 can also includes an activation time calculator 110 that is programmed with a set of equations to compute an activation time for the neighboring points (e.g., for the vertices of the polygon mesh) as a function of the location activation vectors. The activation time calculator 110 can compute activation time, corresponding to the global activation time, for each of the vertices or a selected subset of the vertices on the surface mesh.

By way example, once the local activation vector is computed for each polygon, a time origin is selected. For instance, the time origin can be selected as the location X having the earliest detected activation on the temporal signal (e.g., an electrogram) or another point of reference. From this reference location, the activation time of each neighbor is computed in an iterative manner. This procedure thus can be repeated for each neighboring point over the entire surface mesh or a selected region thereof.

As a further example, for a given point $X_i$ associated with the activation time $T_i$ (e.g., either time t=0, if at the reference location, or another previously calculated activation time), the activation time $T_j$ of its neighbor at location $X_j$ can be represented as follows:

$$T_j = T_i + \frac{\langle \overline{V} | X_j - X_i \rangle}{\|\overline{V}\|}$$

where $\overline{V}$ is the mean activation vector computed from the activation vectors related to the locations $X_i$ and $X_j$.

Figure 8:
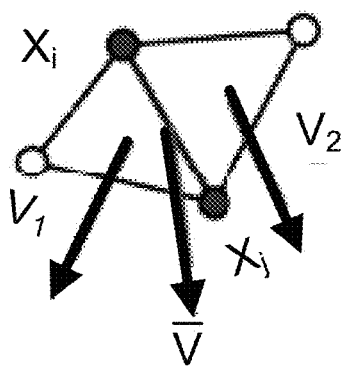
FIG. 8 depicts an example of an aggregate activation vector that can be determined for use in computing an activation time for points on a surface.

For example FIG. 8 demonstrates activation vectors $V_1$ and $V_2$ that can be computed (e.g., by the local activation calculator 108) for two neighboring polygons that are coincident to an edge extending between vertices $X_i$ and $X_j$. The mean activation vector $\overline{V}$ can be computed from $V_1$ and $V_2$.

From the foregoing equation, the mean activation vector $\overline{V}$ is used to compute $T_j$ for location $X_j$ from $T_i$.

As another example, the activation time calculator 110 can employ a set of equations to compute an absolute activation time $T_i$ via global instead of an iterative method. Similar to the iterative approach described above, in order to draw the activation map, each absolute time of activation $T_i$ of each vertex $X_i$ needs to be estimated. The computation of the activation map thus includes estimation of $N_v$ unknowns, such as the $\{T_i\}_{i=1 \ldots N_v}$ where $N_v$ is the number of vertices. The activation times $\{T_i\}_{i=1 \ldots N_v}$ for the $N_v$ vertices can be determined from the $N_e$ time delays, where $N_e$ is the number of edges. It can be shown that whatever the convex 3D surfaces one will have $N_v < N_e$.

Additionally, it will be appreciated that the activation time calculator 110 can also compute the absolute activation time $T_i$ for a subgroup of M of the $N_v$ vertices (M<$N_v$), such as corresponding to a desired surface region of interest. In the example for such a reduced set of vertices, the number of equations to solve is equal to the number of time delays (N') computed between the M selected vertices. For a convex surface, it can also be shown that M<N'.

The activation time calculator 110 thus can be programmed as global method that computes all the $\{T_i\}_{i=1 \ldots N_v}$ concurrently. For example, the global method can employ a global system of equations that links all the unknowns, such as can be a simplest equation that links the two absolute times of activation of two neighboring locations i and j such as can be expressed as a local activation time ($\tau_{ij}$) as follows:

$$T_i - T_j = \tau_{ij}$$

Stated differently, the difference between the two absolute times of activation at two neighboring locations is equal to the time spent to go from one location to the other. This equation can be written for every edge on the surface, and thus the system of equation contains as many equations as the number of edges $N_e$ and $N_v$ unknowns. For example, the matrix for the global system of equations can have the following form:

$$AT=T$$

where:
$T=[T_1, \ldots, T_{N_v}]^T$ is the vector of the unknowns,
$T=[\{\tau_{ij}\}_{1 \ldots N_e}]^T$ the vector of the delays, and
A is the $N_e \times N_v$ matrix of the coefficients.

Additionally, the matrix of coefficients A can be reduced in the example where activation time T is computed for a selected subset of the vertices. For instance, the matrix of coefficients can be computed as (N'×M) to determine the activation time for a subgroup of M vertices, where M corresponds to a selected subset of the $N_v$ vertices.

The rank of A can be equal to $N_v - 1$. However, in practice, the rank of A can be less than $N_v - 1$ because some points of the surface may not be connected to any edge. While each of these non-connected vertices may decrement the rank of A by one, this should not affect the resulting resolution.

Figure 9:
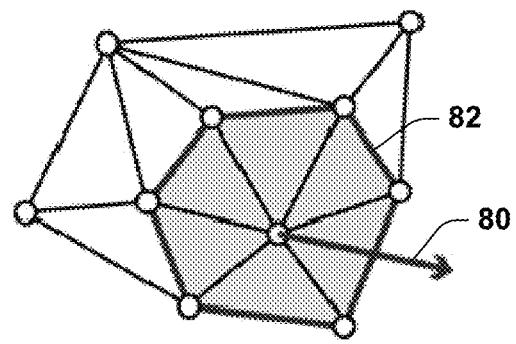
FIG. 9 depicts an example of a local activation vector that can be computed for another polygon on a surface.

As another example, a polygon utilized for computing each local activation vector can include more than three vertices. For instance, the time delays and local activation vectors can be computed over the all vertices of the polygon. FIG. 9 demonstrates an example where a local activation vector 80 is computed (e.g., by the local activation calculators 108) for a polygon based on the time delay (e.g., computed by the time delay calculator 104) for neighboring vertices of a six-sided polygon 82. In this example, the obtained activation vector is centered case centered on a point (e.g., a vertex) inside the polygon.

As mentioned above, the activation time calculation system 100 can employ more than one type activation time calculation, such as employing a hybrid approach that involves a direction activation algorithm, such as mentioned above, in combination with another computation that is selectively applied. The system 100 thus can include a monophasic detection block 112 that can be programmed to find a set of electrograms for which a local activation time can be reliably computed by a second activation time calculator 114. As an example, the second activation time calculator 114 can be programmed to estimate the local activation time by employing a maximum negative derivative function 116 to each of the signals allowed by the detection block 112. Each maximum negative derivative function 116 thus can provide a local activation time, demonstrated as $LAT_1$ through $LAT_K$, for a proper subset of the N points, where typically K<N. In other examples, the maximum negative derivative function 116 can be applied to each of the N points and weighting applied to constrain the linear system S.

The detection block can ascertain the reliability of the second activation time calculator 114 based on evaluating each of the electrogram signals $E_1$ through $E_N$ to predetermined criteria. As an example, the predetermined criteria applied to each signal can be as follows:
1. The second maximum (minimum) of the signal is at least $A_1$ times lower larger than the first maximum (minimum). Maximum values can be used if the signal is positive, and minimum values can be used if the signal is negative.
2. The value of the second maximum of the negative slope is at least $A_2$ times lower than the value of the first maximum value.

The Criteria 1 helps to ensure that a given electrogram does not contain multiple bumps. The Criteria 2 helps to ensure that the maximum dV/dt value is not ambiguous. As one example, $A_1$ can be set to 70% and $A_2$ can be set to 50%. The parameters A1 and A2 can be programmable (e.g., via the user interface 34 of FIG. 1).

The local activation times $LAT_1$ through $LAT_K$ can be applied to constrain the linear system S 106 that solves for the global activation times. By way of example, let $N_v$ be the number of reliable EGMs for which the local activation times (LAT) have been computed; and let $\hat{T}_i$ represent the LAT values. Similar to the non-constrained system mentioned above, the global activation times $G_1$ through $G_N$ can be obtained concurrently or an iterative approach can be employed to provide the activation times.

In one example, since $\hat{T}_i$ has been determined to provide reliable LAT values for a proper subset of the surface points (corresponding to K electrograms), the local activation times $LAT_1$ through $LAT_K$ can constrain the system of equations S by imposing the solution for the global activation time (GAT) to be exactly equal to the $\hat{T}_i$ at these reliable locations. Stated differently, the $LAT_1$ through $LAT_K$ can replace the directional activation values derived from the time delays.

In another example, equations corresponding to the local activation times $LAT_1$ through $LAT_K$ can be added to the original system of equations S which was: $T_j - T_i = \tau_{ij}$ i,j=1 . . . N; i>j where the $T_i$s are the unknowns. This alternative system, which can be denoted S', may contain as many equations as the number of edges of the geometry $N_e$. The corresponding $N_k$ equations can be added to the previous $N_e$ equations: $T_i = \hat{T}_i$, such that S' is composed of ($N_e + N_v$) equations. The new system S' can be solved to obtain the set of global activation times $G_1$ through $G_N$ for the set of surface points. Thus the solution of this new system S' provides a good compromise (e.g., in the least square sense) between the $N_v$ relative delays that link the $T_i$s and the $N_e$ already computed values. That is, in contrast to the previous example, the global activation times for the reliable locations is not necessarily equal to the LAT for these locations.

As demonstrated in the example of FIG. 2, the global activation times $G_1$ through $G_N$ can drive a map generator to provide a corresponding map. The map can be an activation map for one or more selected intervals, such as disclosed herein. Alternatively, the map generator 120 can construct other maps, which can be composite maps displaying activation time information, corresponding to the global activation times $G_1$ through $G_N$, in conjunction with other information.

Figure 10:
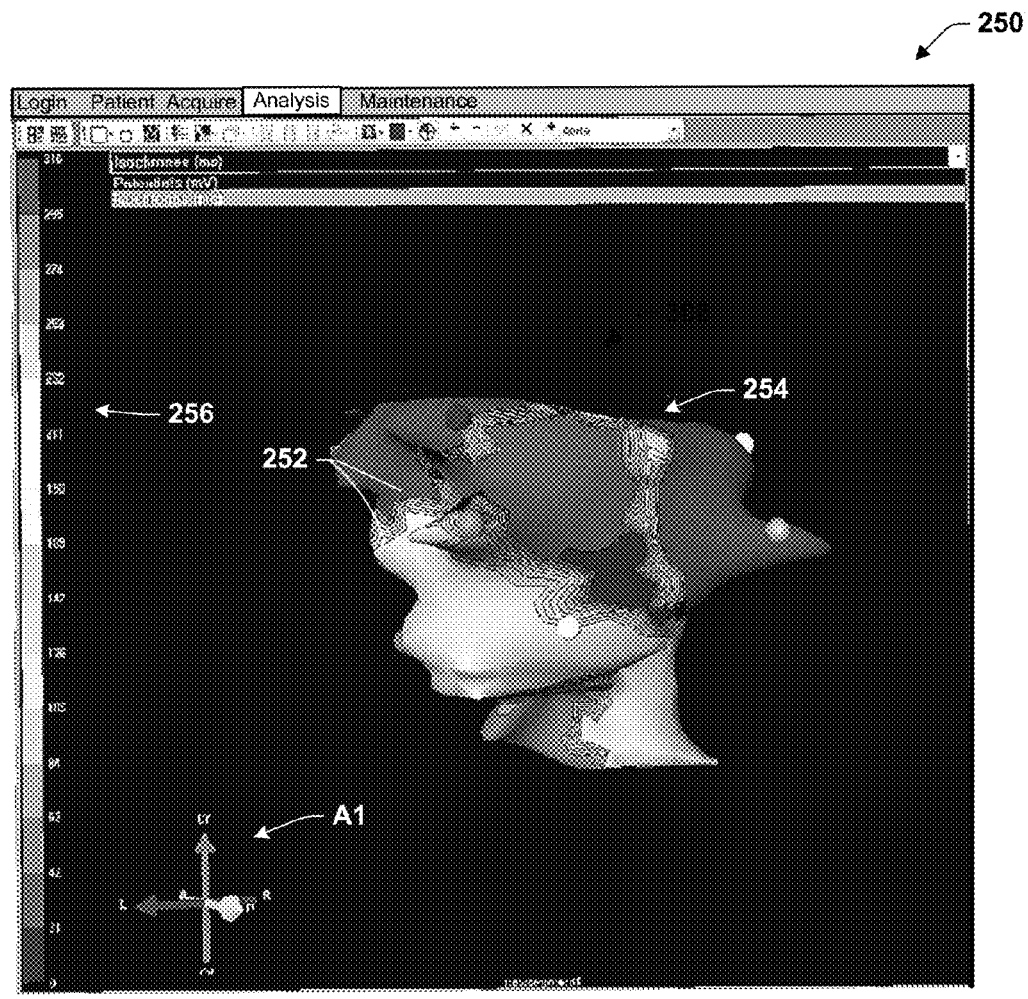
FIG. 10 depicts an example of a graphical user interface demonstrating an activation isochrone map that can be generated.

By way of further example, FIG. 10 depicts an example of a GUI 250 demonstrating a visualization of activation time presented as an isochrone map 252 superimposed over a graphical representation of a surface of a patient's heart 254. Those skilled in the art will understand that various tools and interfaces can be provided for additional analysis and evaluation. Additionally in the example of FIG. 10, a coordinate axis A1 is depicted adjacent to the surface model demonstrating the relative orientation of the patient's heart model 254. A color coded scale demonstrated at 256 can be utilized to identify which color corresponds to what activation times to facilitate review and analysis by a user. A user can further rotate the three-dimensional surface model 254 (e.g., via the cursor or other image controls accessible by the user interface 34 of FIG. 1) to a desired orientation. For instance, the user can rotate the axis A1 or selectively rotate the heart model via a cursor or other user interface controls.

The GUI 250 can also include a mechanism to define a time interval for which activation times can be computed. For example, in response to a user selecting an interval selection user interface element (e.g., a button), a caliper user interface element can be set to define start and stop times, such as relative to user-selected electrogram. In response to such user selection activating the interval selection function, activation times for the surface can be computed according to the selected interval, such as according to the methods shown and described herein. Alternatively, the interval can be computed automatically.

In view of the foregoing, it will be understood that systems and methods can be employed to compute the activation time for a selected beat (e.g., a sinus beat) or an interval that includes less or more than one complete beat. The interval can be selected by the user interface 34 in response to a user input. Alternatively or additionally, the mapping system 22 can automatically identify and select a beat for which activation times will be calculated. As explained herein, the activation time thus can be computed for each of the plurality (e.g., tens, hundreds or thousands) of points on a cardiac surface envelope (e.g., vertices of a polygonal mesh) for the same heart beat or other user prescribed time interval. Additionally, the selected interval can be applied to filter the electroanatomic data such that electroanatomic data is provided for the selected beat.

In one example embodiment, the sampling frequency is 1024 Hz, and the standard activation velocity in a normal tissue around 1 m/s, such that the distance covered during 1 ms is around 1 mm. Therefore, if the mesh surface is very thin, the electrogram signal from one point to its neighbor may be very similar. In some cases, the time delay (e.g., computed by the time delay calculator) between two neighboring EGMs may be equal to or approach zero. Techniques thus can be implemented to reduce the similarity between signals at adjacent vertices, such as the hybrid approach disclosed herein.

As a further example, the electrical signals corresponding to the electroanatomic data at each point $X_i$ can be oversampled to a sampling frequency (e.g. about 100 kHz (102400 Hz)), such as by a cubic spline interpolation. The time delay between electrograms can be computed over this new time scale with an increased resolution of about 0.01 ms, for example.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIG. 11. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 11:
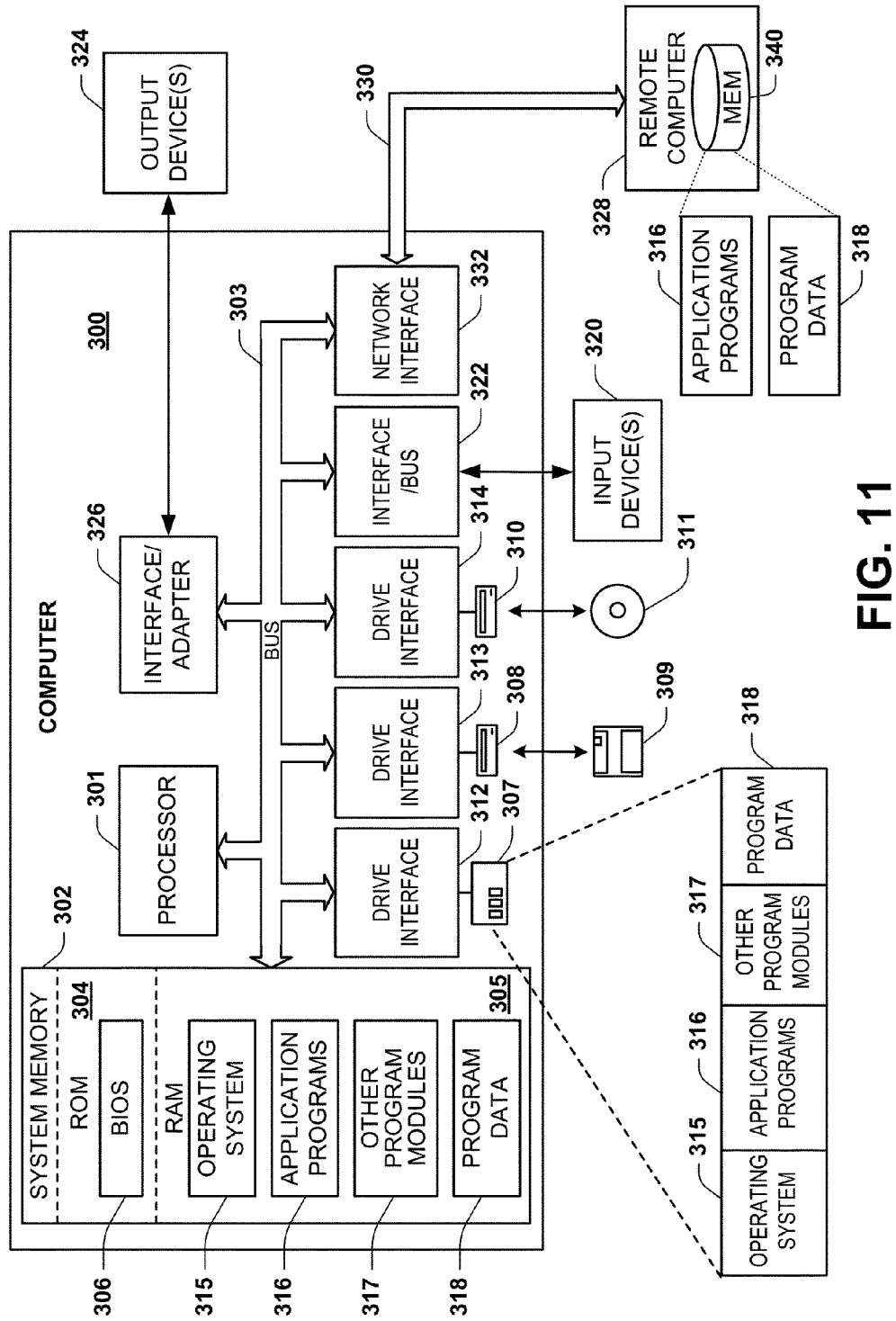
FIG. 11 depicts an example computing environment that can be used to perform methods according to an aspect of the invention.

In this regard, FIG. 11 illustrates one example of a computer system 300 that can be employed to execute one or more embodiments of the invention, such as including acquisition and processing of sensor data, processing of image data, as well as analysis of transformed sensor data and image data associated with the analysis of cardiac electrical activity. Computer system 300 can be implemented on one or more general purpose networked computer systems, embedded computer systems, routers, switches, server devices, client devices, various intermediate devices/nodes or stand alone computer systems. Additionally, computer system 300 can be implemented on various mobile clients such as, for example, a personal digital assistant (PDA), laptop computer, pager, and the like, provided it includes sufficient processing capabilities.

Computer system 300 includes processing unit 301, system memory 302, and system bus 303 that couples various system components, including the system memory, to processing unit 301. Dual microprocessors and other multi-processor architectures also can be used as processing unit 301. System bus 303 may be any of several types of bus structure including a memory bus or memory controller, a peripheral bus, and a local bus using any of a variety of bus architectures. System memory 302 includes read only memory (ROM) 304 and random access memory (RAM) 305. A basic input/output system (BIOS) 306 can reside in ROM 304 containing the basic routines that help to transfer information among elements within computer system 300.

Computer system 300 can include a hard disk drive 307, magnetic disk drive 308, e.g., to read from or write to removable disk 309, and an optical disk drive 310, e.g., for reading CD-ROM disk 311 or to read from or write to other optical media. Hard disk drive 307, magnetic disk drive 308, and optical disk drive 310 are connected to system bus 303 by a hard disk drive interface 312, a magnetic disk drive interface 313, and an optical drive interface 314, respectively. The drives and their associated computer-readable media provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of embodiments shown and described herein.

A number of program modules may be stored in drives and RAM 305, including operating system 315, one or more application programs 316, other program modules 317, and program data 318. The application programs and program data can include functions and methods programmed to acquire, process and display electrical data from one or more sensors, such as shown and described herein. The application programs and program data can include functions and methods programmed to compute activation data and generate one or more activation map for a surface or a portion of a surface, such as shown and described herein.

A user may enter commands and information into computer system 300 through one or more input devices 320, such as a pointing device (e.g., a mouse, touch screen), keyboard, microphone, joystick, game pad, scanner, and the like. For instance, the user can employ input device 320 to edit or modify a domain model. These and other input devices 320 are often connected to processing unit 301 through a corresponding port interface 322 that is coupled to the system bus, but may be connected by other interfaces, such as a parallel port, serial port, or universal serial bus (USB). One or more output devices 324 (e.g., display, a monitor, printer, projector, or other type of displaying device) is also connected to system bus 303 via interface 326, such as a video adapter.

Computer system 300 may operate in a networked environment using logical connections to one or more remote computers, such as remote computer 328. Remote computer 328 may be a workstation, computer system, router, peer device, or other common network node, and typically includes many or all the elements described relative to computer system 300. The logical connections, schematically indicated at 330, can include a local area network (LAN) and a wide area network (WAN).

When used in a LAN networking environment, computer system 300 can be connected to the local network through a network interface or adapter 332. When used in a WAN networking environment, computer system 300 can include a modem, or can be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A system comprising:
a non-transitory memory to store electrical signal data representing electrical signals for a plurality of points distributed across a surface on or within a patient's body and machine-readable instructions; and
a processor to access the non-transitory memory and execute the machine-readable instructions to at least:
select at least a portion of the plurality of points across the surface;
calculate an activation vector for each of the selected plurality of points across the surface based on time delays among respective sets of neighboring signals across the surface according to the electrical signal data for the selected plurality of points;
calculate an activation time for each of the selected plurality of points based on the calculated activation vectors; and
provide an output to display a graphical image for the at least the portion of the plurality of points based on the calculated activation times.

2. The system of claim 1, further comprising a plurality of sensors to measure electrical activity at sensor locations, the electrical signal data being derived from the measured electrical activity.

3. The system of claim 2, wherein the plurality of sensors comprise body surface sensors to non-invasively measure electrical activity across the surface of the patient's body, the processor to execute the instructions to generate the electrical signal data by reconstructing electrical activity on a cardiac envelope within the patient's body with respect to heart based on the measured electrical activity and geometry data.

4. The computer-readable medium of claim 1, wherein the output comprises an isochrone map of the computed activation time.

5. The system of claim 1,
wherein each set of neighboring electrodes is part of a polygon that is part of a mesh surface; and
wherein the activation vector is calculated for each polygon that is part of the mesh surface based on a time delay determined for each adjacent pair of neighboring points in each respective polygon.

6. The system of claim 5, wherein each neighboring electrode represents a vertex of the polygon that is part of the mesh surface.

7. The system of claim 1, wherein the processor further executes the instructions to:
compute the activation vector and the activation time according to a linear system of equations for a directional activation algorithm, and
constrain the linear system of equations based on alternative activation time computations for a proper subset of the plurality points.

8. The system of claim 7, wherein the alternative activation time computations employ a different algorithm from the directional activation algorithm to compute activation times for at least the proper subset of the plurality points.

9. The system of claim 7, wherein the processor further executes the instructions to select the proper subset of the plurality points based on predefined criteria related to reliability of the alternative activation time computations.

10. A device comprising:
a non-transitory memory to store a plurality of electrical signals for points on a surface envelope associated with one of the patient's heart or brain and machine-readable instructions;
a processor to access the non-transitory memory and execute the machine-readable instructions to at least:
selecting electrical data for respective points on the surface envelope corresponding to at least a portion of the plurality of electrical signals;
calculating a direction of activation based on time delays between signals at neighboring point across the surface envelope; and
calculating an activation time for each of the respective points across the surface envelope based on the calculated direction of activation and a time delay between signals at different ones of the respective points; and
generating an activation map to display the calculated activation times for at least a portion of the surface envelope.

11. The device of claim 10, wherein the direction of activation for each respective point across the surface envelope is determined based on a time delay between the electrical signals from each set of neighboring points across the surface envelope.

12. The device of claim 11, wherein the direction of activation is determined locally for each set of neighboring points across the surface envelope.

13. The device of claim 10, wherein the surface envelope corresponds to an epicardial surface or an endocardial surface.

14. The device of claim 10, wherein the surface envelope defines a mesh surface that is divided into polygons in which a respective set of neighboring points define vertices of each respective polygon, the direction of activation being calculated for each polygon based on a time delay determined for each adjacent pair of neighboring points in each respective polygon.

15. The device of claim 14, wherein the processor is further to execute the machine-readable instructions for:
selecting a reference point from the respective points across the surface envelope as a time origin, the activation time being iteratively computed for each of the neighboring points starting at the reference point and moving away from the reference point on the surface envelope.

16. The device of claim 15, wherein the activation time is calculated for each polygon that is part of the mesh surface, and each neighboring electrode represents a vertex of the polygon that is part of the mesh surface.

17. The device of claim 10 wherein the processor is further to execute the machine-readable instructions for:
   computing an activation vector, corresponding to the direction of activation, and the activation time according to a linear system of equations for a directional activation algorithm, and
   constraining the linear system of equations based on alternative activation time computations for a proper subset of the respective points across the surface envelope.

18. The device of claim 17 wherein the processor is further to execute the machine-readable instructions for:
   employing one or more different computations to calculate the alternative activation time computations for a subset of the respective points; and
   aggregating the activation time calculated based on the direction of activation and the alternative activation time computations to provide the activation time for each of the subset of respective points.

19. A method comprising:
   storing, in memory, a plurality of electrograms for respective points across a surface envelope based on measurements of electrical activity by a plurality of sensors;
   calculating, by a system comprising a processor, a direction of activation across the surface envelope based on time delays between electrograms for neighboring points across the surface envelope;
   calculating, by the system, an activation time for each respective point across the surface envelope based on the calculated direction of activation and time delays between the electrograms at different points across the surface envelope; and
   generating an activation map to display the calculated activation times for at least a portion of the surface envelope.

20. The method of claim 19, wherein the activation map is displayed over a representation of a patient's heart.

* * * * *